United States Patent [19]

Phelps et al.

[11] 4,038,752

[45] Aug. 2, 1977

[54] DENTAL ALLOYS

[76] Inventors: Robert Edward Phelps, 73 Chesterton Park, Gloucester; Robin Spill, 44 Kerrs Way; Barry Edward Print, 78 Salisbury Street, both of Wiltshire, all of England

[21] Appl. No.: 645,318

[22] Filed: Dec. 30, 1975

Related U.S. Application Data

[63] Continuation-in-part of Ser. No. 568,284, April 15, 1975, abandoned.

[51] Int. Cl.² ............................................. A61C 13/00
[52] U.S. Cl. .................................................. 32/2; 32/8
[58] Field of Search .................. 75/171, 170; 148/32, 148/32.5; 32/2, 8

[56] References Cited

U.S. PATENT DOCUMENTS

| | | | |
|---|---|---|---|
| 2,864,696 | 12/1958 | Foreman | 75/171 |
| 3,437,480 | 4/1969 | Cape | 75/171 |
| 3,761,728 | 9/1973 | Kochavi | 75/171 |

*Primary Examiner*—Robert Peshock
*Attorney, Agent, or Firm*—Dennison, Dennison, Meserole & Pollack

[57] ABSTRACT

A corrosion-resistant dental prosthesis that consists of a nickel-base alloy with significant quantities of chromium, silicon, manganese and boron.

9 Claims, No Drawings

DENTAL ALLOYS

This is a continuation-in-part of application Ser. No. 568,284, filed Apr. 15, 1975.

This invention relates to dental prosthesis alloys and particularly to nickel base alloys containing substantial amounts of nickel and chromium for use in restorative dentistry procedures as an alternative to gold alloys.

For an alloy to be suitable for dental purposes, it must be non-toxic and resistant to oxidation during heating, melting and casting so that it may be soldered and bonded to porcelain. Also, if it is to be used to make dental inlays, crowns and bridges, it must be ductile and have low hardness and high burnishability. Known dental alloys contain substantial amounts of cobalt and chromium but these have the disadvantage that they have a relatively-high coefficient of expansion and casting shrinkage.

Nickel-base alloys are known for use as hard facing alloys characterized by extreme hardness and attendant brittleness. Their hardness and brittleness render them substantially incapable of being wrought or machined except to a very limited extent. U.S. Pat. Nos. 2,864,696 issued Dec. 16, 1958 to Forman and 3,437,480 issued Apr. 8, 1969 to Cape are considered representative of such hard facing alloys. It will be appreciated that the properties of these alloys render them unsuitable for the use disclosed herein where high burnishability, low hardness and ductility are essential to the fabrication of dental inlays, crowns, and bridges.

The present invention aims at providing an improved dental prosthesis alloy, and accordingly provides a dental alloy having the following composition:

| Constituent | % by weight of alloy |
| --- | --- |
| Carbon | up to 0.25 |
| Chromium | 10.0 – 25.0 |
| Silicon | 0.5 to 7.5 |
| Manganese | 0.1 to 1.5 |
| Iron | up to 3.0 |
| Boron | 0.1 to 0.6 |
| Copper | up to 3.0 |
| Nickel | Balance |

The invention will now be described in further detail by way of example.

Since the alloy must be easy to solder and bond to ceramic materials, the degree of surface oxidation during melting and casting must be low. To ensure this, it is essential that the alloy should contain small amounts of silicon, manganese and boron. The presence of these elements also helps to maintain good fluidity of the alloy. The alloy must also be corrosion resistant and because of this, a minimum quantity of chromium is essential. If it is desirable that the alloy should be more resistant to corrosion by chlorides, a small amount of copper should also be included.

Alloys of the following composition have been found to be particularly suitable for dental applications:

| Constituents | % by weight of alloy |
| --- | --- |
| Carbon | up to 0.15 |
| Chromium | 10.0 to 20.0 |
| Silicon | 0.5 to 4.0 |
| Manganese | 0.1 to 1.0 |
| Iron | up to 3.0 |
| Boron | 0.1 to 0.6 |
| Copper | up to 2.0 |
| Nickel | Balance |

EXAMPLE 1

An alloy of the present invention which is particularly well adapted for use in the preparation of bridgework, and for bonding with ceramic materials such as porcelain, has the following composition:

| Constituents | % by weight of alloy |
| --- | --- |
| Carbon | up to 0.15 |
| Chromium | 15.0 to 20.0 |
| Silicon | 3.0 to 4.0 |
| Manganese | 0.5 to 1.0 |
| Iron | up to 3.0 |
| Boron | 0.3 to 0.6 |
| Nickel | Balance |

This alloy is non-toxic and can be easily melted and cast due to its oxidation resistance and fluidity. It has a high tensile and yield strength when cold and is reasonably ductile. Its density is relatively low compared with gold and the gold alloys which are usually used in dental work.

EXAMPLE 2

An alloy of the present invention for use in making crowns and inlays has the following composition:

| Constituents | % by weight of alloy |
| --- | --- |
| Carbon | up to 0.15 |
| Chromium | 15.0 to 17.0 |
| Silicon | 1.0 to 2.0 |
| Manganese | 0.5 to 1.0 |
| Iron | up to 1.0 |
| Boron | 0.1 to 0.4 |
| Nickel | Balance |

This alloy also is non-toxic and can be easily melted and cast. It has low hardness and excellent burnishability which are two of the properties needed if an alloy is to be used for making inlays and crowns. It also has a low casting shrinkage, which characteristic is necessary if an alloy is to be used in making inlays.

Other examples of alloys of the present invention which are particularly useful in dental work have the following compositions.

EXAMPLE 3

| Constituents | % by weight of alloy |
| --- | --- |
| Carbon | up to 0.15 |
| Chromium | 10.0 to 15.0 |
| Silicon | 3.0 to 4.0 |
| Manganese | 0.5 to 1.0 |
| Iron | up to 3.0 |
| Boron | 0.1 to 0.4 |
| Nickel | Balance |

EXAMPLE 4

| Constituents | % by weight of alloy |
| --- | --- |
| Carbon | up to 0.15 |
| Chromium | 15.0 to 20.0 |
| Silicon | 3.0 to 4.0 |
| Manganese | 0.5 to 1.0 |
| Iron | up to 3.0 |
| Boron | 0.1 to 0.4 |
| Nickel | Balance |

EXAMPLE 5

| Constituents | % by weight of alloy |
|---|---|
| Carbon | up to 0.15 |
| Chromium | 15.0 to 17.0 |
| Silicon | 0.5 to 1.0 |
| Manganese | 0.5 to 1.0 |
| Iron | up to 1.0 |
| Boron | 0.3 to 0.6 |
| Nickel | Balance |

EXAMPLE 6

| Constituents | % by weight of alloy |
|---|---|
| Carbon | up to 0.15 |
| Chromium | 15.0 to 20.0 |
| Silicon | 3.0 to 4.0 |
| Manganese | 0.5 to 1.0 |
| Iron | up to 3.0 |
| Boron | 0.3 to 0.6 |
| Copper | 1.0 to 2.0 |
| Nickel | Balance |

EXAMPLE 7

| Constituents | % by weight of alloy |
|---|---|
| Carbon | up to 0.15 |
| Chromium | 15.0 to 17.0 |
| Silicon | 1.0 to 2.0 |
| Manganese | 0.5 to 1.0 |
| Iron | up to 1.0 |
| Boron | 0.1 to 0.4 |
| Copper | 1.0 to 2.0 |
| Nickel | Balance |

All of these alloys are non-toxic and they may be used in restorative dentistry procedures as an alternative to gold alloys.

We claim:

1. A dental prosthesis of an alloy consisting essentially of:

| Constituent | % by weight of alloy |
|---|---|
| Carbon | up to 0.25 |
| Chromium | 10.0 to 25.0 |
| Silicon | 0.5 to 7.5 |
| Manganese | 0.1 to 1.5 |
| Iron | up to 3.0 |
| Boron | 0.1 to 0.6 |
| Copper | up to 3.0 |
| Nickel | Balance |

2. A dental prosthesis as claimed in claim 1, consisting essentially of:

| Constituent | % by weight of alloy |
|---|---|
| Carbon | up to 0.15 |
| Chromium | 10.0 to 20.0 |
| Silicon | 0.5 to 4.0 |
| Manganese | 0.1 to 1.0 |
| Iron | up to 3.0 |
| Boron | 0.1 to 0.6 |
| Copper | up to 2.0 |
| Nickel | Balance |

3. A dental prosthesis as claimed in claim 1 consisting essentially of:

| Constituent | % by weight of alloy |
|---|---|
| Carbon | up to 0.15 |
| Chromium | 15.0 to 20.0 |
| Silicon | 3.0 to 4.0 |
| Manganese | 0.5 to 1.0 |
| Iron | up to 3.0 |
| Boron | 0.3 to 0.6 |
| Nickel | Balance |

4. A dental prosthesis as claimed in claim 1 consisting essentially of:

| Constituent | % by weight of alloy |
|---|---|
| Carbon | up to 0.15 |
| Chromium | 15.0 to 17.0 |
| Silicon | 1.0 to 2.0 |
| Manganese | 0.5 to 1.0 |
| Iron | up to 1.0 |
| Boron | 0.1 to 0.4 |
| Nickel | Balance |

5. A dental prosthesis as claimed in claim 1 consisting essentially of:

| Constituent | % by weight of alloy |
|---|---|
| Carbon | up to 0.15 |
| Chromium | 15.0 to 20.0 |
| Silicon | 3.0 t0 4.0 |
| Manganese | 0.5 to 1.0 |
| Iron | up to 3.0 |
| Boron | 0.1 to 0.4 |
| Nickel | Balance |

6. A dental prosthesis as claimed in claim 1 consisting essentially of:

| Constituent | % by weight of alloy |
|---|---|
| Carbon | up to 0.15 |
| Chromium | 15.0 to 17.0 |
| Silicon | 0.5 to 1.0 |
| Manganese | 0.5 to 1.0 |
| Iron | up to 1.0 |
| Boron | 0.3 to 0.6 |
| Nickel | Balance |

7. A dental prosthesis as claimed in claim 1 consisting essentially of:

| Constituent | % by weight of alloy |
|---|---|
| Carbon | up to 0.15 |
| Chromium | 15.0 to 20.0 |
| Silicon | 3.0 to 4.0 |
| Manganese | 0.5 to 1.0 |
| Iron | up to 3.0 |
| Boron | 0.3 to 0.6 |
| Copper | 1.0 to 2.0 |
| Nickel | Balance |

8. A dental prosthesis as claimed in claim 1 consisting essentially of:

| Constituent | % by weight of alloy |
|---|---|
| Carbon | up to 0.15 |
| Chromium | 15.0 to 17.0 |
| Silicon | 1.0 to 2.0 |
| Manganese | 0.5 to 1.0 |
| Iron | up to 1.0 |
| Boron | 0.1 to 0.4 |
| Copper | 1.0 to 2.0 |
| Nickel | Balance |

9. A dental prosthesis as claimed in claim 1 consisting essentially of:

| Constituent | % by weight of alloy |
|---|---|
| Carbon | up to 0.15 |
| Chromium | 10.0 to 15.0 |
| Silicon | 3.0 to 4.0 |
| Manganese | 0.5 to 1.0 |
| Iron | up to 3.0 |
| Boron | 0.1 to 0.4 |
| Nickel | Balance |

* * * * *